(12) United States Patent
Baker et al.

(10) Patent No.: US 7,222,526 B2
(45) Date of Patent: May 29, 2007

(54) LIQUID MEASUREMENTS USING CAPACITIVE MONITORING

(75) Inventors: Lemont Baker, Minneapolis, MN (US); Muhidin Lelic, Manchester, CT (US)

(73) Assignee: Ortho-Clinical Diagnostics, Inc, Rochester, NY (US)

( * ) Notice: Subject to any disclaimer, the term of this patent is extended or adjusted under 35 U.S.C. 154(b) by 78 days.

(21) Appl. No.: 10/870,090

(22) Filed: Jun. 17, 2004

(65) Prior Publication Data

US 2005/0279855 A1    Dec. 22, 2005

(51) Int. Cl.
    *G01F 23/26* (2006.01)
(52) U.S. Cl. .................. 73/304 C; 73/290 R; 73/304 R
(58) Field of Classification Search .............. 73/290 R, 73/304 C, 304 R
    See application file for complete search history.

(56) References Cited

U.S. PATENT DOCUMENTS

| | | | | |
|---|---|---|---|---|
| 4,326,851 A | * | 4/1982 | Bello et al. | 73/304 C |
| 4,347,741 A | * | 9/1982 | Geiger | 73/304 C |
| 4,736,638 A | * | 4/1988 | Okawa et al. | 73/864.24 |

(Continued)

FOREIGN PATENT DOCUMENTS

| | | |
|---|---|---|
| EP | 0806672 A2 | 11/1997 |
| EP | 1091198 A1 | 4/2001 |
| EP | 1209471 A2 | 5/2002 |
| EP | 1 361 443 A | 12/2003 |
| JP | 132084 A | 8/1982 |
| JP | 10 311840 A | 11/1998 |
| JP | 283150 A | 12/2005 |
| WO | WO 98/57132 | 12/1998 |
| WO | WO 2004/027375 A2 | 4/2004 |

OTHER PUBLICATIONS

European Search Report for European Application No. EP 05 25 3762, dated Jun. 08, 2006, The Hague.

*Primary Examiner*—Hezron Williams
*Assistant Examiner*—Rodney Frank
(74) *Attorney, Agent, or Firm*—Todd J. Burns

(57) ABSTRACT

An apparatus for determining the volume of liquid in a probe tip of an aspirating or dispensing probe, such as those used in a diagnostic analyzer, includes: two electrodes on opposite sides of the probe tip and the electrodes and liquid form a variable capacitor; a resistor; a voltage source and the electrodes and resistor are in electrical communication in at least one of series, parallel or series and parallel to form an RC circuit; and a microprocessor in electrical communication with the RC circuit for converting an electrical signal to a volume of liquid in the probe tip. In a preferred embodiment, the probe tip is separate from the probe and is adapted to be fitted on the end of a probe for aspirating and dispensing a liquid. In another preferred embodiment, the apparatus further includes a solenoid, and the voltage source, electrodes, resistor, and solenoid are in electrical communication in at least one of series, parallel or series and parallel to form an RLC circuit, and the microprocessor is in electrical communication with the RLC circuit for converting an electrical signal to a volume of liquid in the probe tip. The apparatus can be used with a liquid have a known or unknown dielectric constant and can be used to determine the presence of bubbles in the liquid.

17 Claims, 11 Drawing Sheets

U.S. PATENT DOCUMENTS

| | | | |
|---|---|---|---|
| 4,794,085 A | 12/1988 | Jessop et al. | |
| 4,897,244 A | 1/1990 | Wallace et al. | |
| 5,012,496 A * | 4/1991 | Weinreb et al. | 377/21 |
| 5,045,286 A * | 9/1991 | Kitajima et al. | 422/100 |
| 5,104,621 A * | 4/1992 | Pfost et al. | 422/67 |
| 5,152,424 A * | 10/1992 | Weinreb et al. | 222/1 |
| 5,304,347 A * | 4/1994 | Mann et al. | 422/67 |
| 5,443,791 A | 8/1995 | Cathcart et al. | |
| 5,450,743 A | 9/1995 | Buote | |
| 5,493,922 A * | 2/1996 | Ramey et al. | 73/863.02 |
| 5,582,798 A | 12/1996 | Meltzer | |
| 5,639,426 A * | 6/1997 | Kerr et al. | 422/100 |
| 5,648,727 A * | 7/1997 | Tyberg et al. | 324/677 |
| 6,121,049 A | 9/2000 | Dorenkott et al. | |
| 6,148,666 A * | 11/2000 | Roesicke | 73/290 R |
| 6,158,269 A | 12/2000 | Dorenkott et al. | |
| 6,250,130 B1 | 6/2001 | Howard et al. | |
| 6,317,696 B1 | 11/2001 | Clements et al. | |
| 6,484,556 B1 | 11/2002 | Jabobs et al. | |
| 6,551,558 B1 * | 4/2003 | Mann et al. | 422/100 |
| 6,663,353 B2 * | 12/2003 | Lipscomb et al. | 417/63 |
| 2003/0022380 A1 | 1/2003 | Jakubowicz et al. | |
| 2003/0104634 A1 | 6/2003 | Jacobs et al. | |
| 2003/0200801 A1 * | 10/2003 | Lipscomb et al. | 73/290 V |
| 2004/0067164 A1 | 4/2004 | Van Brunt et al. | |
| 2004/0232075 A1 * | 11/2004 | Wells | 210/636 |

* cited by examiner

Tip Capacitance for Various Liquid Volumes and Dielectrics

Tip Capacitance for Various Liquid Volumes and Dielectrics

US 7,222,526 B2

LIQUID MEASUREMENTS USING CAPACITIVE MONITORING

BACKGROUND OF THE INVENTION

1. Field of the Invention

The present invention relates to measuring aspects of a liquid by determining the capacitance of a volume of liquid. More particularly, the present invention relates to using capacitance in a dispensing or aspirating probe, particularly in automated analyzers, such as chemistry or blood analyzers, to determine the volume of liquid in the probe tip or the presence of air bubbles in the liquid in the probe tip.

2. Description of the Related Art

Advances in industries utilizing chemical and biological processes have created a need for the ability to accurately and automatically dispense varying quantities of liquids for commercial, laboratory, and research uses, particularly in automated analyzers. Typically, an automated analyzer includes an automated liquid metering system that automatically aspirates a sample of liquid from a reservoir or test-tube containing patient sample and dispenses the liquid into another vessel, such as a reaction cuvette. The liquid moving system typically includes a pipette or probe that accomplishes the aspirate and dispensing functions under the control of a robotic arm.

Automated analyzers are widely employed in blood bank centers, hospitals, and clinical laboratories. Tests utilizing chemical reagents specific to the test being conducted (i.e. HCV, HIV) are dispensed into another container, e.g., a reaction chamber containing the sample to be tested (serum, plasma, blood). The resulting reaction products that arise are subsequently analyzed (i.e. luminescence, optical properties, electrical properties) and results are generated. Typically the results are stored electronically and printed out for review.

Monitoring and controlling aspiration or dispensing of a liquid is known in the art. Several methods and techniques exist for doing the same. For example, U.S. Pat. No. 6,158,269 uses a pressure based technique. Pressure is monitored (air or fluid column) using a pressure transducer and the data collected are then quantified and used to make determinations as to the state of fluid. U.S. Pat. No. 4,794,085 discloses using a vacuum to determine when a probe is approaching and has contacted a liquid to be aspirated.

Other methods include optical measurement systems which quantify the optical index change characteristics of a liquid system to verify when liquid has been dispensed. Other known optical approaches entail using an optical path (beam) which when broken corresponds to liquid being dispensed.

Other publications for monitoring and controlling aspirating or dispensing include U.S. Pat. Nos. 6,250,130, 5,450,743, 6,121,049, 5,443,791, 6,317,696, 5,045,286 and EP Patent Application No. 1209471 A2.

The use of capacitance and other methods to measure an aspect of a liquid is also known in the art. Liquid level methods are used to sense the liquid level in a container and then determine the quantity of liquid in the container based on its geometry. As stated above, liquid level methods are implemented using various technologies (capacitive, optical, pressure). Examples of capacitive determination of liquid levels includes WO 98/57132 and EP 1091198 A1. Other uses of capacitance are described in U.S. Pat. No. 4,897,244 which discloses the use of capacitance to determine when a probe contacts a liquid.

Much of the known art only controls the proximity of the metering probe to the surface of the liquid to be aspirated. These methods and techniques, however, do not measure the actual volume of liquid that is aspirated or dispensed. This is generally done indirectly. That is, many known aspirating and dispensing probes uses a syringe pump coupled to a stepper motor to aspirate or dispense a liquid. The volume of liquid aspirated or dispense is determined by the number of steps performed by the stepper motor. This will generally result in an accurate determination of liquid volume as long as what is being dispensed or aspirated is truly liquid. Problems can arise if, for example, the probe is not fully immersed in the liquid or if there are air bubble(s) entrained in the liquid. Both of these conditions can result in air volume being read as liquid volume, thus leading to less liquid being aspirated or dispensed than was intended. Accurate metering of liquid is important in applications such as diagnostic analyzers or blood analyzers.

Other problems associated with much of the known art include lack of robustness of the device used to monitor and control aspiration and dispense. That is, many of the known systems are susceptible to mechanical vibrations and other perturbations. Yet other problems lie in the size of the systems to monitor aspiration and dispense in that known systems often require components away from the aspirating probe and probe tip. For example, U.S. Pat. Nos. 6,158,269 and 6,484,556 require a pressure transducer between the stepping motor and the probe. For the foregoing reasons, there is a need for increased improvement in the measurement of liquid being aspirated or dispensed. There is also a need for an increased improvement in the robustness or reliability of a system or apparatus to make such measurements and in consolidating the components for such measurement in a central location, preferably at the point the measurement is taken.

SUMMARY OF THE INVENTION

The present invention is directed to a method that solves the foregoing problems of improving the measurement of a liquid being aspirated or dispensed by a probe, particularly by directly measuring the amount of liquid in a tip or probe and increasing the reliability of the system, as well increasingly consolidating the components of the system nears the probe or probe tip where the measurement is being taken.

One aspect of the invention is directed to an apparatus for determining the volume of liquid in a probe tip of an aspirating or dispensing probe, which includes: two electrodes on opposite sides of the probe tip and the electrodes and liquid form a variable capacitor; a resistor; a voltage source and the electrodes and resistor are in electrical communication in at least one of series, parallel or series and parallel to form an RC circuit; and a microprocessor in electrical communication with the RC circuit for converting an electrical signal to a volume of liquid in the probe tip. In a preferred embodiment, the probe tip is separate from the probe and is adapted to be fitted on the end of a probe for aspirating and dispensing a liquid.

In another preferred embodiment, the apparatus further includes a solenoid, and the voltage source, electrodes, resistor, and solenoid are in electrical communication in at least one of series, parallel or series and parallel to form an RLC circuit, and the microprocessor is in electrical communication with the RLC circuit for converting an electrical signal to a volume of liquid in the probe tip.

According to another aspect of the invention, there has been provided a method for determining the volume of liquid having a known dielectric constant in a probe tip of an aspirating or dispensing probe. The method includes: providing the apparatus described above; providing a liquid in the probe tip having a known dielectric constant; applying a known voltage (Ug) from the voltage source; easuring the voltage (U1) from the capacitor; determining the capacitance (C1) of the variable capacitor; and determining the volume (V2) of the liquid based on the capacitance (C2) and dielectric constant ∈ of the liquid.

According to another aspect of the invention, there has been provided, a method for determining the volume of liquid having a unknown dielectric constant in a probe tip of an aspirating or dispensing probe. The method includes providing the apparatus described above; providing a database or calibration curve of known capacitances versus known volumes for the liquid being measured or dispensed; providing the liquid in the probe tip; applying a known voltage (Ug) from the voltage source; measuring the voltage (U1) from the capacitor; determining the capacitance (C1) of the variable capacitor; comparing the capacitance (C1) with the known capacitances and volumes in the calibration curve or database; determining the volume of the liquid based on the comparison f the capacitance (C1) and the known capacitance.

According to another aspect of the invention, there has been provided according to another aspect of the invention, a method for determining the presence of bubbles in a probe tip or if a desired volume of liquid is in the probe tip of an aspirating or dispensing probe. The method includes: determining a reference capacitance (C1) of the desired volume of liquid (V1); providing the apparatus described above; providing a volume (V2) of liquid in the probe tip; applying a known voltage (Ug) from the voltage source; measuring the voltage from the capacitor (U2); determining the capacitance (C2) of the variable capacitor with volume (V2); comparing the determined capacitance (C2) with the reference capacitance (C1); and generating an error signal if the difference between the reference and determined capacitance exceeds a predetermined amount.

According to another aspect of the invention there has been provided an apparatus for dispensing or aspirating a liquid. The apparatus includes: a probe; a probe tip adapted to fit on a first end of the probe to be inserted into a source of liquid; at least one of a vacuum or pressure source in fluid communication with the probe to produce a pressure differential with respect to ambient pressure, sufficient to at least one of aspirate or dispense a liquid respectively; and the apparatus for determining the volume of liquid in a probe tip as described above.

According to another aspect of the invention, there has been provided an analyzer for analyzing an analyte in a sample. The analyzer includes: a sample supply; a metering station for metering sample from the sample supply into or onto a test element, wherein the metering station comprises the apparatus for determining the volume of liquid in a probe tip of an aspirating or dispensing probe as described above; and a measurement station for measuring a property of the sample.

Yet another aspect of the invention provides: a method for dispensing and aspirating a selected volume of a liquid. The method includes: providing a container containing the liquid to be aspirated; providing a probe having a vacuum and pressure source in fluid communication with the probe to produce a pressure differential with respect to ambient pressure, sufficient to aspirate and dispense the liquid, said probe being mounted for movement towards and away from the container; providing a probe tip adapted to fit on a first end of the probe to be inserted into the liquid; providing the apparatus for determining the volume of liquid in a probe tip as described above; moving the probe in a direction towards the container until the distal end of probe tip is immersed in the liquid; aspirating a volume (V1) of liquid into the probe tip; determining the capacitance (C1) of the variable capacitor; and determining the volume (V2) of the liquid based on the capacitance (C2) and dielectric constant ∈ of the liquid.

According to another aspect of the invention, the methods described above are implemented by a computer program interfacing with a computer. Another aspect of the invention provides an article of manufacture comprising a computer usable medium having computer readable program code configured to conduct the methods described above.

Further objects, features and advantages of the present invention will be apparent to those skilled in the art from detailed consideration of the preferred embodiments that follow.

DETAILED DESCRIPTION OF PREFERRED EMBODIMENTS

Figure 1A:
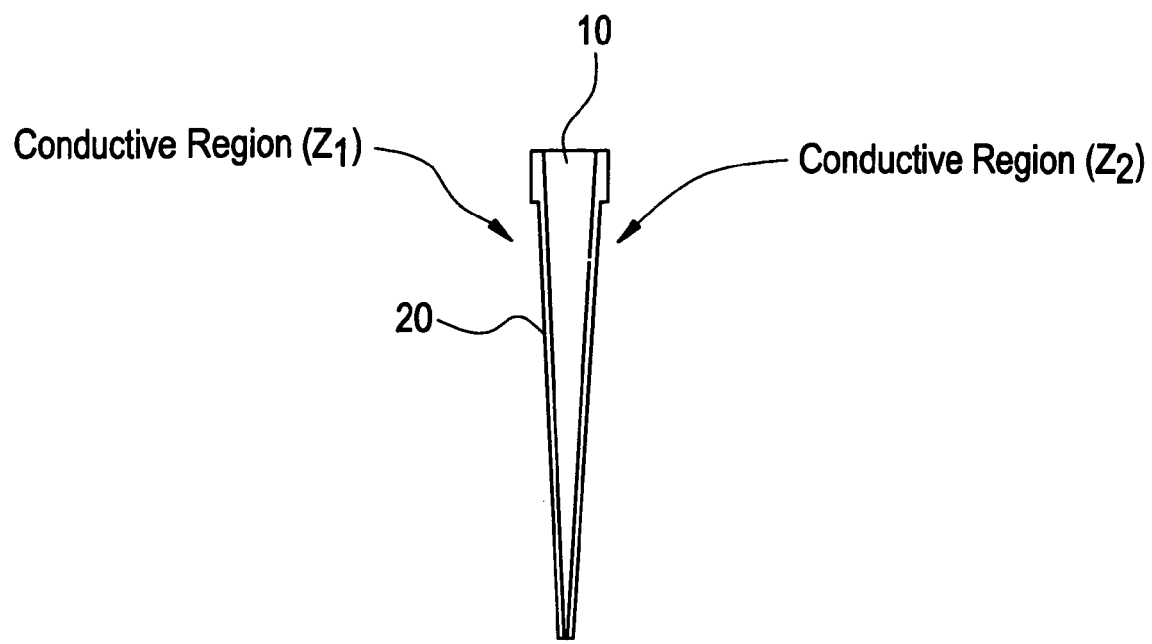
FIG. 1A shows a schematic side view of a probe tip with electrically conductive electrodes acting as plates in a capacitor circuit.

The present invention broadly relates to an apparatus and method for determining the volume of a liquid in the probe tip of a liquid aspiration and dispense probe. In the present invention, the probe tip is designed to act as a variable capacitor. When liquid is aspirated and/or dispensed, the varying volume alters the capacitance sensed in the disposable tip. The capacitance changes can be used to determine if liquid is present or not in the tip, and to determine the volume of liquid based on the dielectric properties of the liquid and the total capacitance value.

In other words, the present invention relies upon the relationship (described more fully below) between capacitance and the type and amount of material (i.e., liquid)

between the electrodes of the capacitor. The amount will be related to the volume of liquid in the probe tip. The type of liquid (i.e., its dielectric constant) may or may not be known. If the dielectric constant is known, then determining volume based on a capacitance measurement is relatively straightforward as explained below. If the dielectric constant is not known, then determining volume will still be possible using calibration curves that plot volume vs. capacitance of that liquid or similar liquids.

A unique feature of the present invention is the ability to monitor the volume of liquid based on the total capacitance of the liquid, particularly for monitoring liquids being aspirated and dispensed. This allows direct monitoring of the liquid volume, as opposed to indirect monitoring, such as with a stepper motor described above. Another advantage of the present invention is that the apparatus is more self contained and can be independent of mechanical systems (pumps/motors, etc.). Thus, the present invention including the capacitive probe tip, along with supporting electronics can be outfitted to fit numerous liquid handling applications. Another advantage resulting from the features of the present invention, particularly the lack of moving parts or sensitive electronics, is that the reliability of monitoring liquid volume will be increased, particularly against mechanical vibrations. Still another advantage is increased throughput of aspirating and dispensing processes, since the volume is being determined during the process. That is, the volume can be directly determined in real time during the metering event as opposed to indirectly, such as through pressure sensing. This allows the process (e.g., an assay procedure) to be adjusted immediately, e.g., amounts of reagents or sample can be adjusted to account for more or less liquid being aspirated than originally intended, as opposed to determining an error downstream in the process and having to discard and re-run the process.

The apparatus for determining the volume of liquid includes electrodes on opposite sides of the probe tip. The probe tip can be either disposable or fixed, preferably disposable (due to cross-contamination issues of fixed tips). Known disposable tips are those used with the Vitros® line of diagnostic analyzers manufactured by Ortho-Clinical Diagnostics, Inc. In a preferred embodiment, the tip is modified and outfitted with two conductive regions (i.e., electrodes) embedded and insulated on the exterior or interior surface of the tip. Such a tip can be made by methods known in the art, such as insert molding, where a metal electrode is inserted into a mold for a tip and the tip is then formed by injection molding. Alternatively, the tips can be formed with molded holes or columns into which electrodes can be placed. To prevent shorting, the electrodes should be insulated from touching the liquid being metered. The conductive regions are charged/discharged accordingly and a corresponding capacitance can be measured.

Figure 1B:
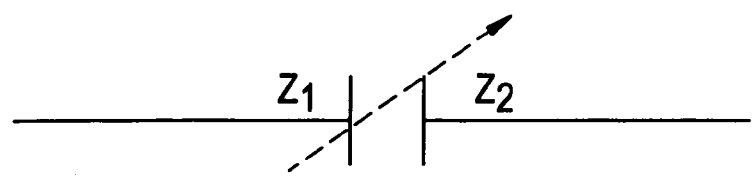
FIG. 1B shows an electrical schematic of the tip in FIG. 1B.

As described above, the electrodes and liquid between the electrodes form a variable capacitor. FIG. 1 illustrates the concept. In FIG. 1A, reference numerals Z1 and Z2 are variables which represent a conductive region 20 that varies depending on the level of the liquid in the probe tip 10. Since the conductive region and amount of dielectric liquid between the conductive region will vary depending on the amount of liquid in the tip, the capacitance will also vary. FIG. 1B, is an electrical schematic of the capacitor shown in FIG. 1B.

Figure 9:
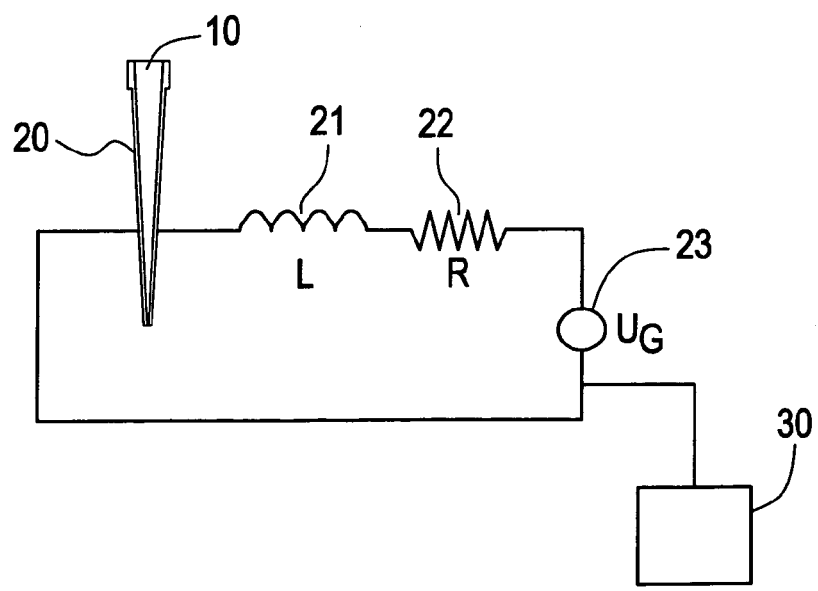
FIG. 9 shows an RLC circuit with the probe tip and electrodes as the capacitor.

The apparatus also includes a resistor 22, optionally a solenoid 21, and a voltage source 23 as shown in FIG. 9. These components individually are well known in the art. The electrodes, resistor, solenoid are electrically connected. The configuration of the circuit can be series, parallel or combinations of series and parallel to form an RC (without the solenoid) or preferably an RLC circuit. In the embodiment shown in FIG. 9, the elements of the circuit are arranged in series.

A microprocessor in electrical communication with the RC or RLC circuit for converting an electrical signal to a volume of liquid in the probe tip is also provided. This is shown schematically in FIG. 9 as 30. The microprocessor can also provide feedback to the controlling mechanism of the probe tip (such as a stepper motor for a piston pump) to control the amount of liquid being aspirated or dispensed depending the actual volume of liquid being detected by the apparatus of the present invention.

As briefly described above, the capacitance will depend on the volume of liquid in the tip and the dielectric value of the liquid in the tip. This relationship can be shown as:

$$C = \frac{\varepsilon_0 \varepsilon_r S}{d} \quad (1)$$

where C=Capacitance (F)
$\varepsilon_0$=8.854×10$^{-12}$ (F/m)
$\varepsilon_r$=dielectric constant
S=surface area (m$^2$) of the electrodes
d=distance (m) between the electrodes Capacitance can be calculated by methods known in the art. See, e.g., U. S. Inan, A. S. Inan, "Engineering Electromagnetics", Addison-Wesley, Section 4.9, 1999 and Z. Gajic, "Linear Dynamic Systems and Signals", Prentice Hall, Upper Saddle River, 2002, both of which are incorporated by reference in their entireties.

Figure 2A:
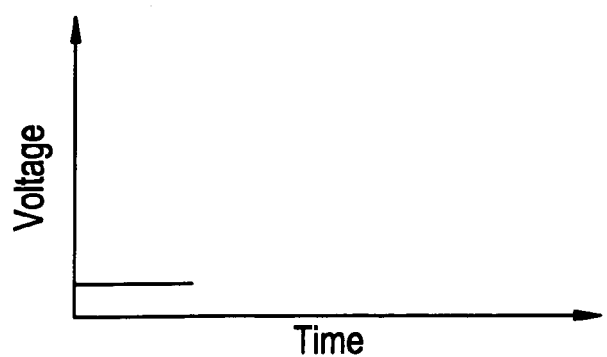
FIGS. 2–7 show the amount of liquid in a probe tip (FIGS. 2B–7B) and the corresponding voltage (FIGS. 2B–7B).
Figure 2B:
Figure 3A:
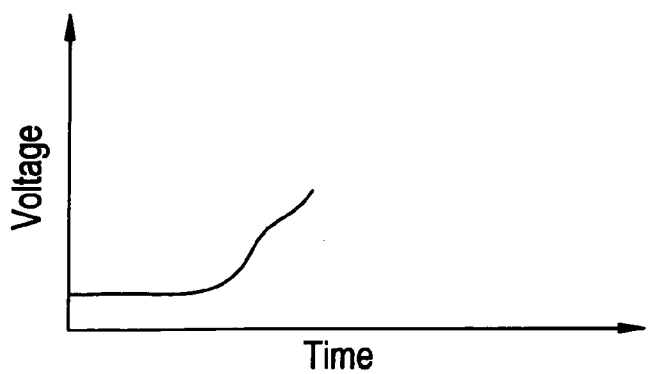
Figure 3B:
Figure 4A:
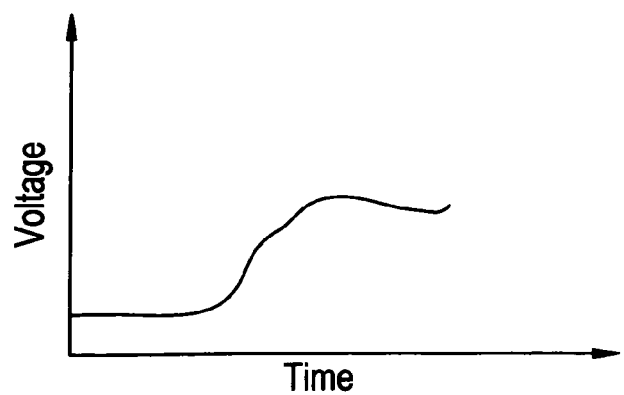
Figure 4B:
Figure 5A:
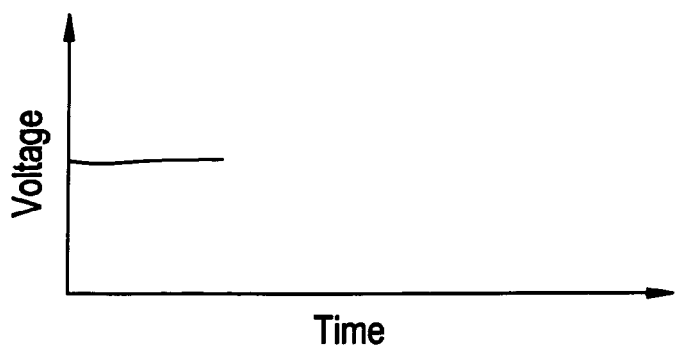
Figure 5B:
Figure 6A:
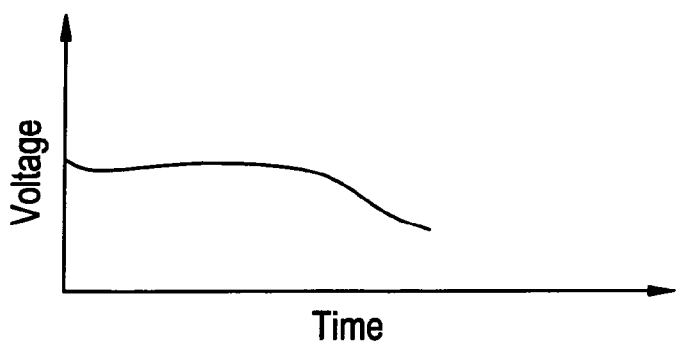
Figure 6B:
Figure 7A:
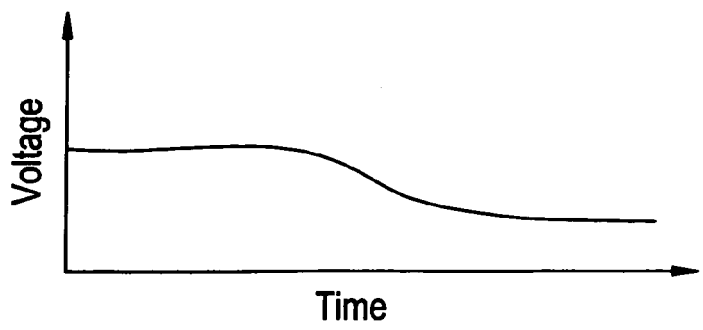
Figure 7B:

Initially the tip is filled with air which has a dielectric constant of ~1. After the tip is filled with liquid a change in capacitance occurs due to the difference in dielectric constant of the liquid (e.g. blood $\varepsilon_r$~50) relative to air. From equation 1 it is apparent that C is related directly to $\varepsilon_r$. Assuming a fixed surface area (S), fixed distance (d), the capacitance changes are directly related to changes in the dielectric $\varepsilon_r$. For most metering (alternatively referred to as "pipetting") applications the liquids being metered (e.g., aspirated and/or dispensed) are reagents and blood products (serum and plasma) that have $\varepsilon_r$ much greater than air. FIGS. 2A–7B illustrate expected data (capacitance signals expressed as voltage which is inversely proportional to capacitance) that would occur throughout a metering cycle and the corresponding state of liquid in the tip. FIGS. 2A, 3A, 4A are signals expected to be sensed during aspiration, whereas FIGS. 2B, 3B and 4B shows the status of the liquid in the tip. FIGS. 5A, 6A, 7A depict signals expected to be sensed during dispense, whereas FIGS. 5B, 6B and 7B shows the status of the liquid in the tip. Thus, FIGS. 2A–7B depict the information that can be obtained from the variable capacitance tip of the present invention.

Figure 8:
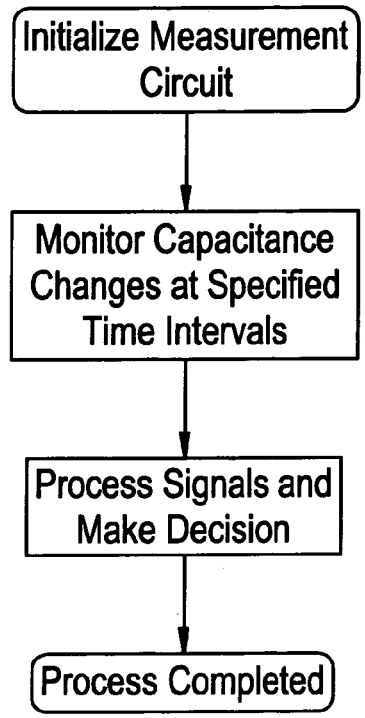
FIG. 8 shows a flowchart utilizing the present invention to monitor an aspirating and dispense process.

One embodiment of the present invention is demonstrated in the block diagram (FIG. 8). In this approach the capacitance is measured directly while metering events (i.e., aspirating and/or dispensing) are occurring. This allows for direct, real-time processing of capacitance changes and subsequent decisions or rules can be incorporated to monitor the viability of a metering event. That is, based on the capacitance being measured in real time, the microprocessor can control the probe being used to aspirate or dispense the liquid. This is a significant advantage over the known art that monitored metering precision and accuracy after the dispense and/or aspiration.

In a preferred embodiment an electrical circuit is provided that includes a tip placed between two conductive electrodes, optionally a solenoid with inductance L, and a resistor R. As described above, a tip with electrodes behaves as a variable capacitor, C. These two or three components form an RC or RLC circuit, respectively, which can be arranged in series (preferred embodiment shown in FIG. 9), in parallel, or as other serial/parallel combinations. This circuit is connected to a source of voltage, such as an alternative current (AC) generator. The values of R, L and frequency of the AC generator can be adjusted by those skilled in the art based on the specific application and by the guidance of the present application.

If an empty tip is placed between the capacitor electrodes or electrodes are placed on the exterior of the tip, its capacitance will be $C_0$. When a certain amount of liquid is aspirated in the tip, the capacitance of the capacitor will increase to C.

The impedance of the RLC circuit from FIG. 9 can be represented (in the Laplace or s-domain) as $$\frac{V(s)}{I(s)} = X(s) = R + sL + \frac{1}{sC}$$

where
V(s)=Laplace or s-domain voltage
I(s)=Laplace or s-domain current
X(s)=Laplace or s-domain impedance
s=Laplace or s-domain
L=inductance
C=capacitance
R=resistance In order to identify/measure the presence of liquid and bubbles in the tip, one can measure the change of the voltage at one of the elements of the RLC circuit. Measuring the voltage change on the capacitor results in the format:

$$U_c(s) = \frac{1}{LCs^2 + RCs + 1} U_g(s) \quad (2)$$

In frequency domain (when s is replaced with jω), this voltage will have the format:

$$U_c(j\omega) = \frac{1}{(1 - LC\omega^2) + j\omega RC} U_g(j\omega) \quad (3)$$

Since an amplitude change of the voltage $|U_c(j\omega)|$ is of interest, formula (3) can be represented as:

$$|U_c(j\omega)| = \frac{1}{\sqrt{(1 - LC\omega^2)^2 + (\omega RC)^2}} \cdot |U_g(j\omega)| \quad (4)$$

This voltage amplitude will depend on the circular frequency ω of the generator $U_g(j\omega)$ and it will have a maximum value. This maximum value will occur at $$\omega = 1/\sqrt{LC} \quad (5)$$

So, from (4) and (5) there is:

$$|U_c(j\omega)|_{max} = \frac{1}{\sqrt{\left(\frac{1}{\sqrt{LC}} RC\right)^2}} \cdot |U_g(j\omega)| = \left(\frac{1}{R}\sqrt{\frac{L}{C}}\right) \cdot |U_g(j\omega)| \quad (6)$$

Figure 10:
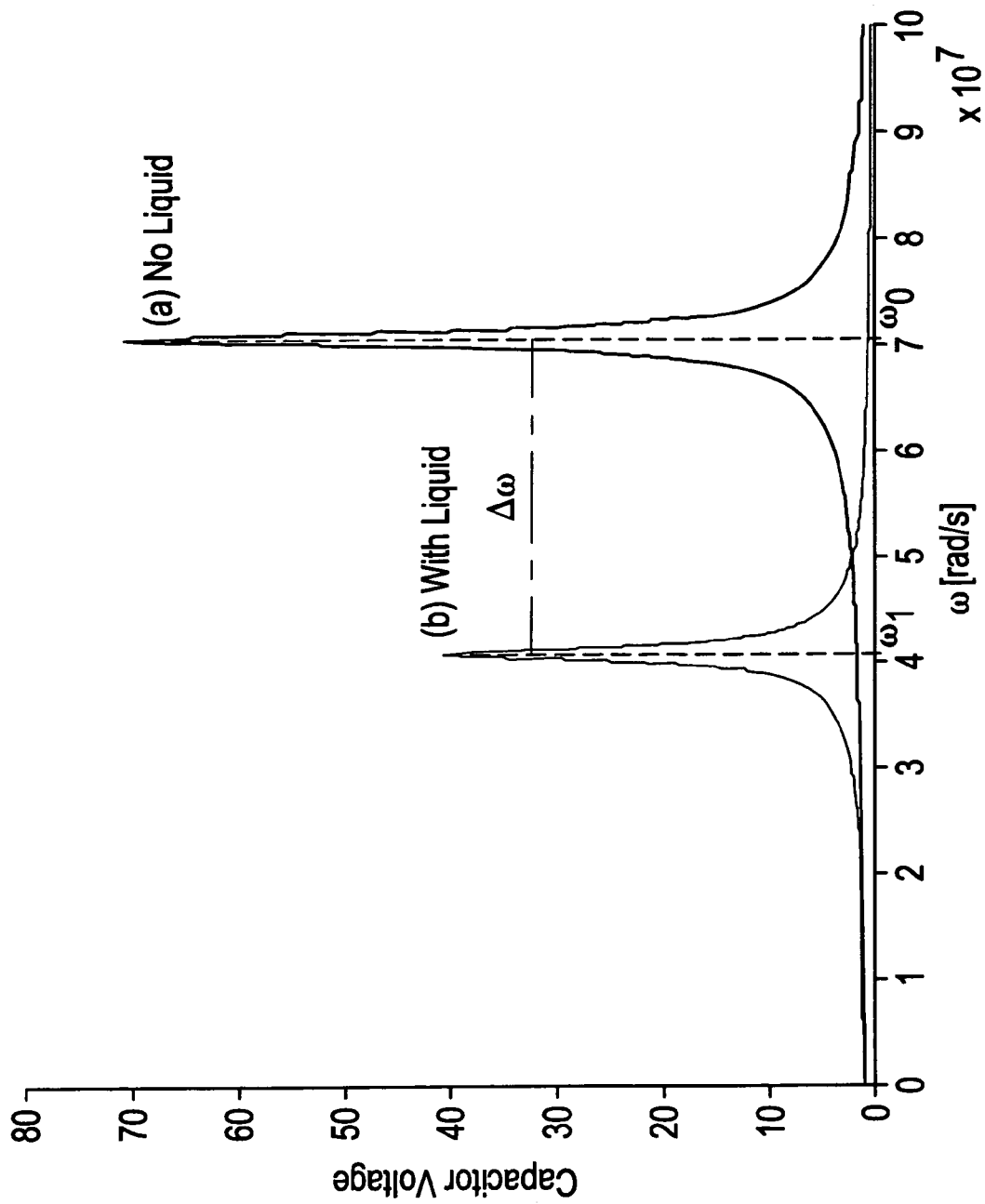
FIG. 10 shows a graph of the frequency dependence of $|U_c(j\omega)|$ for two cases: (a) the tip is empty (capacitance $C_0$) and (b) the tip contains some liquid, possible with bubbles (capacitance C).

FIG. 10 shows the frequency dependence of $|U_c(j\omega)|$ for two cases: (a) the tip is empty (capacitance $C_0$) and (b) the tip contains some liquid, possible with some bubbles (capacitance C).

The voltage maximum shifts to the left (towards lower frequencies) when the tip contains liquid. This feature can be utilized to sense the amount and type of liquid as well as the presence of bubbles in the same.

For an empty tip, formulae (5) and (6) become:

$$\omega_0 = 1/\sqrt{LC_0} \quad (7)$$

$$|U_c(j\omega_0)|_{max} = \left(\frac{1}{R}\sqrt{\frac{L}{C_0}}\right) \cdot |U_g(j\omega_0)| \quad (8)$$

The circular frequency $\omega_0$ can be determined experimentally by changing the frequency of generator, $U_g(j\omega)$, until the amplitude of the capacitor voltage $|U_c(j\omega)|$ reaches its maximum. After that, capacitance of $C_0$ can be calculated from (7) as $$C_0 = \frac{1}{L\omega_0^2} \quad (9)$$

Once $C_0$ is calculated, capacitance and hence volume for tips with any other liquid type can be calculated by those skilled in the art. In the present invention two accurate preferred methods are proposed: (i) employing the voltage peaks, and; (ii) employing voltage drop at $\omega_0$. These methods are described below. Both of these methods assume that the dielectric constant of the liquid volume being measured is known, either by calibration curves or from a reference source.

I. Employing Shift of Voltage Peaks

Assume that the tip contains some liquid with volume $V_i$ and dielectric constant ∈. The capacitance of the tip with this liquid will be $C_i$. It can be calculated as follows:

1. Decrease the oscillation frequency of input voltage $U_g(j\omega)$ until the voltage $|U_c(j\omega)|$, measured at the end of the tip capacitor reaches its maximum, $|U_c(j\omega)|_{max}$ (see FIG. 10). Let this circular frequency be $\omega_i$.

2. Calculate the capacitance of the tip with liquid from formula (6) as:

$$|U_C(j\omega_i)|_{max} = \left(\frac{1}{R}\sqrt{\frac{L}{C_i}}\right) \cdot |U_g(j\omega_i)| \quad (10)$$

Since the amplitude of the input voltage is constant ($|U_g(j\omega_0)|=|U_g(j\omega_i)|$), the capacitance of tip with the liquid can be calculated from the ratio of (8) and (10):

$$\frac{|U_C(j\omega_i)|_{max}}{|U_C(j\omega_0)|_{max}} = \frac{\left(\frac{1}{R}\sqrt{\frac{L}{C_i}}\right)\cdot|U_g(j\omega_i)|}{\left(\frac{1}{R}\sqrt{\frac{L}{C_0}}\right)\cdot|U_g(j\omega_0)|} = \sqrt{\frac{C_0}{C_i}} \quad (11)$$

3. From (11), the capacitance is obtained as:

$$C_i = C_0 \cdot \left(\frac{|U_C(j\omega_0)|_{max}}{|U_C(j\omega_i)|_{max}}\right)^2 \quad (12)$$

II. Employing Voltage Drop at $\omega_0$

In this method the frequency of input voltage remains constant and the capacitance of the tip with the liquid $C_i$ is calculated from the ratio of the capacitor voltages with the liquid in the tip, $|U_c(j\omega_0)|$ and the maximum capacitor voltage when the tip is empty, $|U_c(j\omega_0)|_{max}$. From (4), (7), and (8) the result is:

$$\frac{|U_C(j\omega_0)|_{max}}{|U_C(j\omega_0)|} = \frac{\left(\frac{1}{R}\sqrt{\frac{L}{C_0}}\right)\cdot|U_g(j\omega_0)|}{\frac{1}{\sqrt{(1-\omega_0^2 LC_i)^2 + \omega_0^2 R^2 C_i^2}}\cdot|U_g(j\omega_0)|} \quad (13)$$

$$= \left(\frac{1}{R}\sqrt{\frac{L}{C_0}}\right)\cdot\sqrt{\left(1-\frac{LC_i}{LC_0}\right)^2 + \frac{R^2 C_i^2}{LC_0}}$$

The value of the capacitance of the tip with the liquid, obtained from (13) is:

$$C_i = \frac{1+\sqrt{\frac{R^2 C_0}{L}\cdot\left[\left(\frac{|U_C(j\omega_0)|_{max}}{|U_c(j\omega)|}\right)^2 \cdot\left(1+\frac{R^2 C_0}{L}\right)-1\right]}}{1+\frac{R^2 C_0}{L}} \quad (14)$$

In this method the formula (14) for calculation of $C_i$ is more complex than formula (12) from Method I, but it has the advantage in that it does not require a variable frequency input voltage generator.

Once the tip capacitance $C_i$ is known, then the relationship between tip capacitance and tip volume can be determined. Assume that the total volume of the tip is $V_0$. Then, any amount of liquid in the tip can be represented as V=k V$_0$, where k is an element of the closed interval [0, 1] (15)

The capacitance of the tip with unknown amount of liquid is equal to V can be represented as:

$C_i = k \cdot d \cdot C_0 + (1-k) \cdot C_0$ (16)

The first term ($k \cdot d \cdot C_0$) in formula (16) represents the capacitance of the part of the tip filled with liquid, and second part represents the capacitance corresponding to the part of the tip filled with air. The dielectric constant $\in$ characterizes the type of the liquid in the tip. Then, from (15) and (16) it is straightforward to find the relationship between the volume of the liquid and the tip capacitance:

$$V = \frac{C_i/C_0 - 1}{d-1}\cdot V_0 \quad (17)$$

Note that (17) represents a linear relationship. Thus, volume is linearly proportional to capacitance. The capacitance of the tip with liquid will depend on the following:

volume of the liquid in the tip type of the liquid (dielectric constant) in the tip. As described above, both of these methods assume that the dielectric constant of the liquid being measured is known.

A preferred method of using the present invention for monitoring the volume of liquid in the tip, when the dielectric constant is not known and the presence (and amount) of bubbles is described below.

Figure 11:
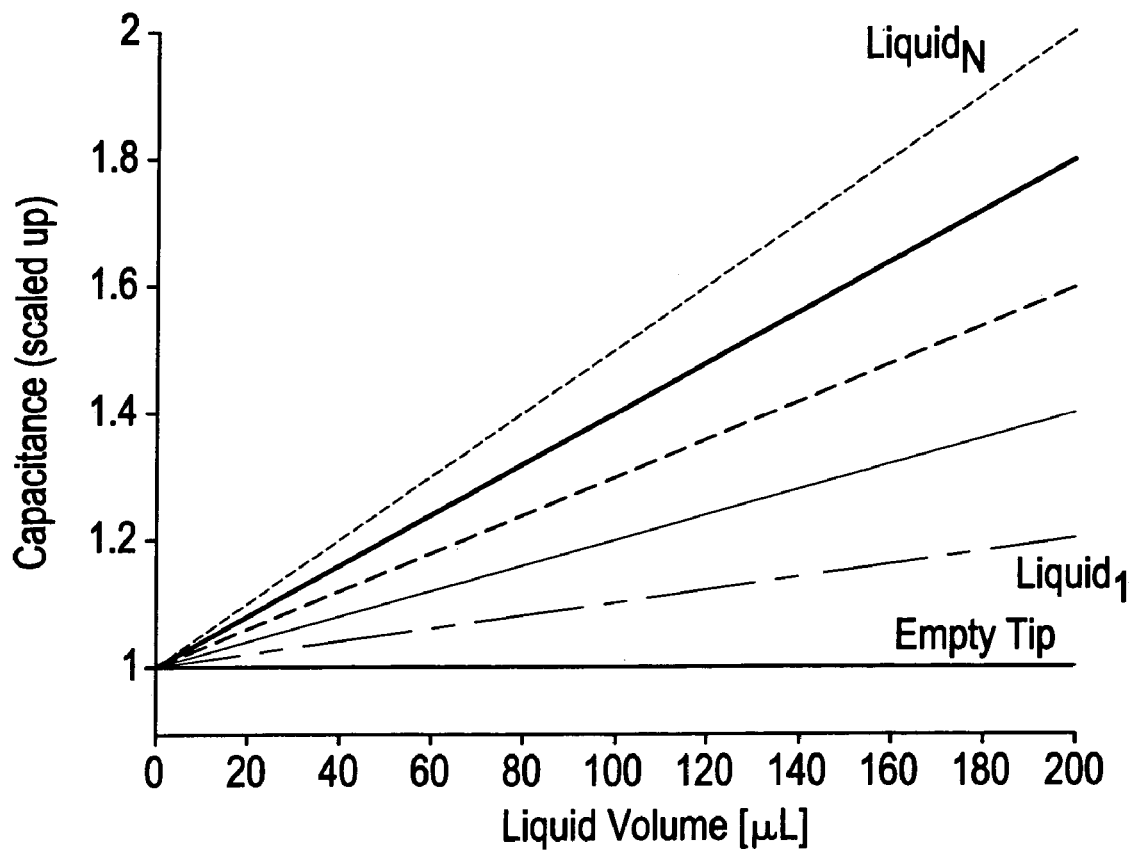
FIG. 11 shows calibration curves for various liquids plotting capacitance vs. volume.

First, a calibration curve is developed for the particular liquid having its volume measured. To do this, the volume of the same liquid is varied and for each volume the capacitance of the tip with liquid is measured. It is important to ensure no bubbles are in the liquid. The measured capacitances and volumes pairs (V,C) are saved, e.g., in the memory of the microprocessor unit. If additional liquids are to be measured, the above procedure can be repeated for different liquids having different dielectric constants. FIG. 11 shows calibration curves for various liquids. These calibration curves can be stored and serve as reference values in automated high-speed liquid aspiration/dispensing. Assuming the dielectric constant of the liquid being aspirated/dispensed is known (from construction of a calibration curve as described herein), these calibration curves can be used to detect the error in volume of liquid aspirated in the tip. This error can be attributed either to the presence of bubbles in the liquid or as an indicator of incorrect measuring of liquid volume.

Figure 12:
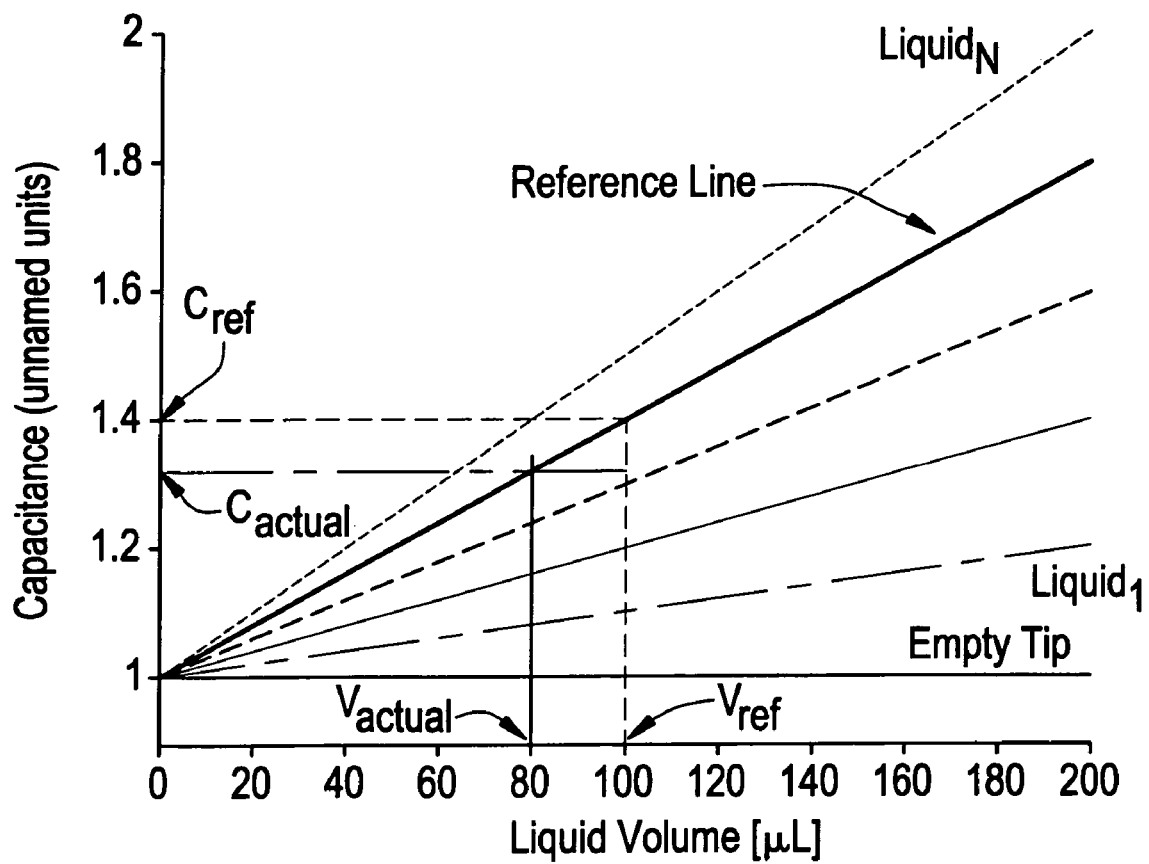
FIG. 12 shows a graphical representation for determining an error in a liquid being aspirated.

FIG. 12 shows an example where 100 μL of liquid is required to be aspirated into the tip. According to the calibration curve, that amount of liquid would result in the capacity $C_{ref}$ of 1.4 (unnamed units). However, since in this example the aspirated liquid contains bubbles, the capacitance of the liquid will be reduced to $C_{actual}$. When this capacity is projected on the reference line, it will show the actual volume of the liquid in the tip, which in this case would be 80 μL. It means that there is an aspiration error of 20 μL. As can be seen from the example above, determining sample volume, sampling error and the presence of bubbles in the liquid can be readily determined using the present invention.

As noted above, the major advantage over conventional methods is that the present invention can monitor liquid being aspirated and dispensed solely in the tip. Another advantage is that the change in capacitance is used to establish validity of aspiration and/or dispense. Even if dielectric properties (i.e., the dielectric constant) of the liquid are not known, one can still monitor/measure the volume of liquid being aspirated using the calibration curves described above.

Another advantage of the invention is that liquid level detection can be implemented by virtue of monitoring the peak value of the waveform measured. The waveform is the whatever (voltage, capacitance, etc.) characteristic being measured against time. A sudden change indicates that the tip has entered/left a foreign substance (i.e., indicates that the tip has contacted liquid).

In one embodiment, where the liquid is water, the range of the tip capacitance spans, approximately, from 2 pF (for empty tip) to 15 pF (for the tip filled with water). For a tip filled with other liquids this capacitance would have a different value.

Described below is a preferred algorithm for implementing a liquid dispense operation.

Algorithm 1: Liquid Dispensing

Input Data: Initial Volume $V_{init}$ is known.

Figure 13:
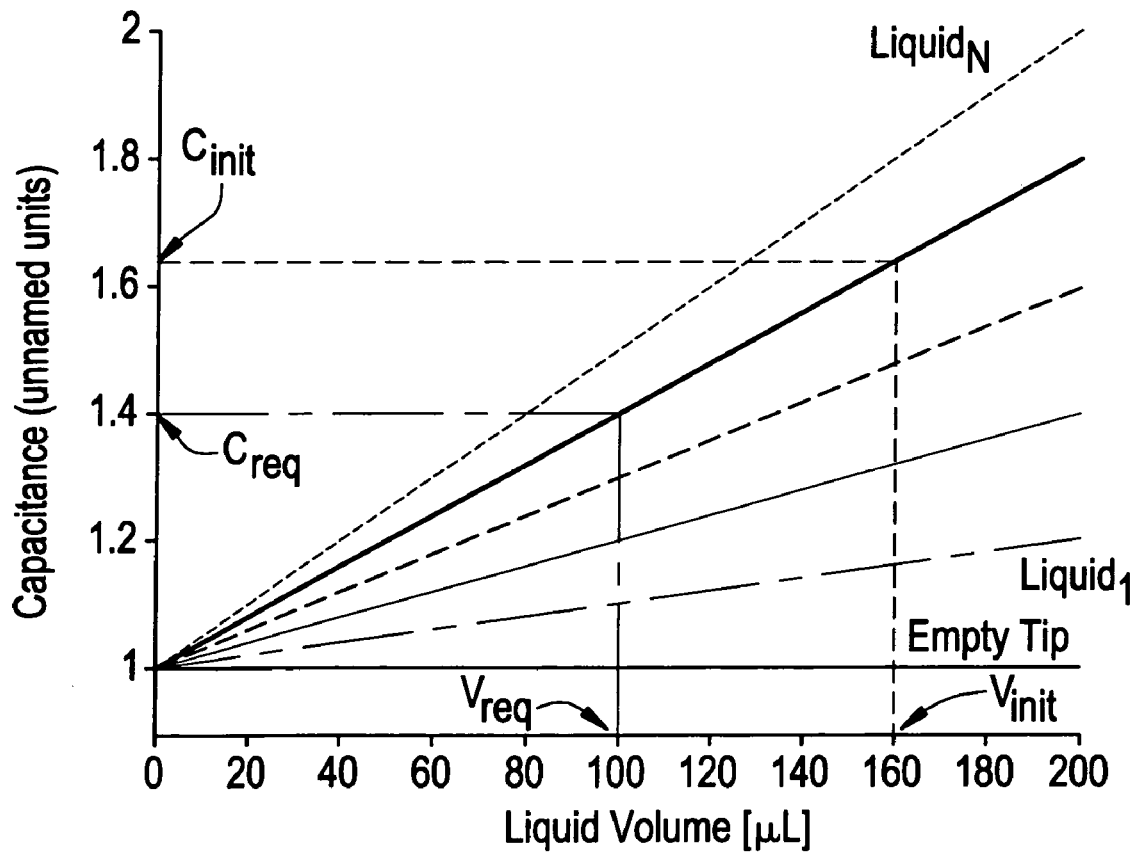
FIG. 13 is a graph for graphically illustrating a dispense process according to a preferred embodiment.
Figure 14:
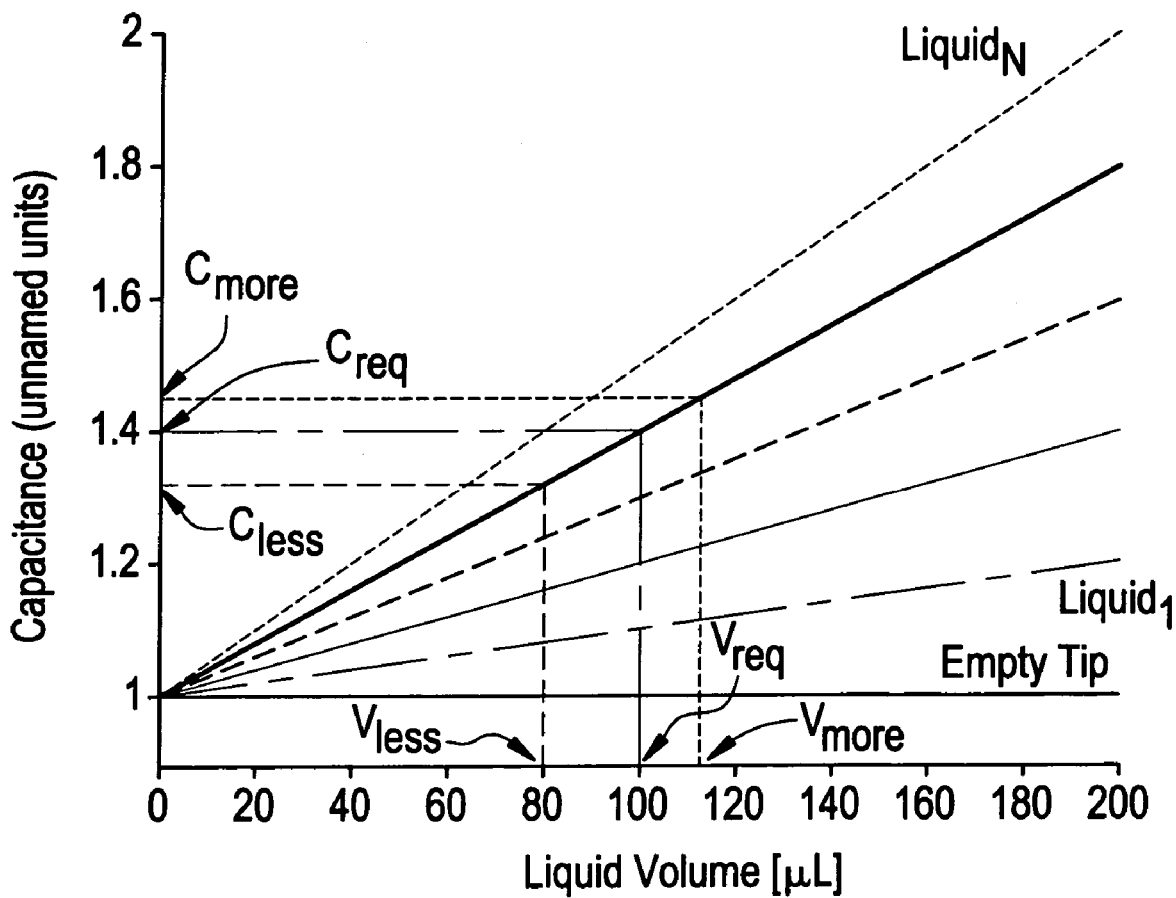
FIG. 14 is a graph for graphically illustrating an aspirating process according to a preferred embodiment.

Calculate initial capacitance $C_{init}$ from the calibration line (FIG. 13) or lookup table, prepared earlier.

Select volume to be dispensed, $V_{disp}$.

Calculate the new target volume $V_{req}$ and target capacitance, $C_{req}$:

$$V_{req} = V_{init} - V_{disp} \quad (20)$$

Target capacitance is calculated from the calibration line of lookup table

Start dispensing liquid from the tip. At the same time, monitor the difference between the actual capacitance, $C_{actual}$ and target capacitance, $C_{req}$:

$$\in_{disp} = C_{actual} - C_{req} \quad (21)$$

Stop dispensing when the error $\in_{disp}$ smaller than some pre-specified acceptable value $\delta$.

In the algorithm above, actual capacitance, $C_{actual}$ can be calculated by either employing shift of voltage peaks (equation (12) from above), or by the voltage drop method (equation (14) from above).

Described below is a preferred algorithm for liquid aspiration with error detection and correction.

Algorithm 2: Liquid Aspiration

Select type of liquid and volume to be aspirated, $V_{req}$. Find the target capacitance, $C_{req}$ from the calibration curve or lookup table.

Aspirate the required volume.

Using one of the methods described above (i.e., shift of voltage peaks (equation (12), or voltage drop method (equation (14)), calculate the actual capacitance, $C_{actual}$.

Calculate the actual voltage $V_{actual}$ from the calibration curve (FIG. 9) or lookup table.

Calculate the error $$\in_{asp} = V_{req} - V_{actual} \quad (22)$$

If the error $|\in_{asp}| < \delta$ ($\delta$ is a small acceptable value) stop, otherwise continue.

If $\in_{asp} < 0$ (i.e. $V_{req} < V_{actual}$), more liquid was aspirated then required. Apply Algorithm 1 to dispense the excessive liquid.

If $\in_{asp} > 0$ (i.e. $V_{req} > V_{actual}$), insufficient amount of liquid was aspirated. There are bubbles present. Volume of bubbles is equal to $$\Delta V = V\text{req} - V\text{actual} \quad (23)$$

Go to step 2 to correct this error.

Figure 16:
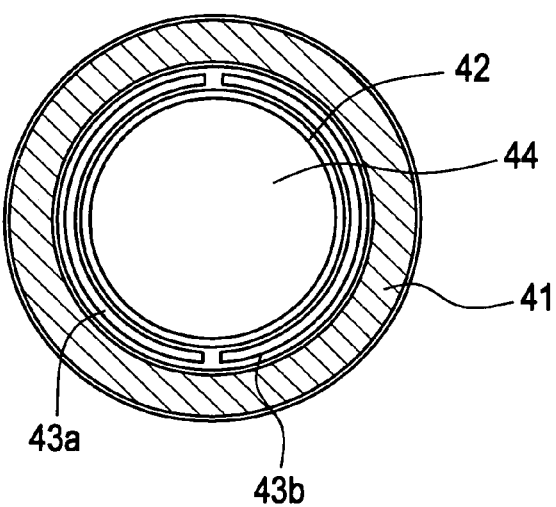
FIG. 16 is a top view of the probe tip and solenoid combination shown in FIG. 15.
Figure 17:
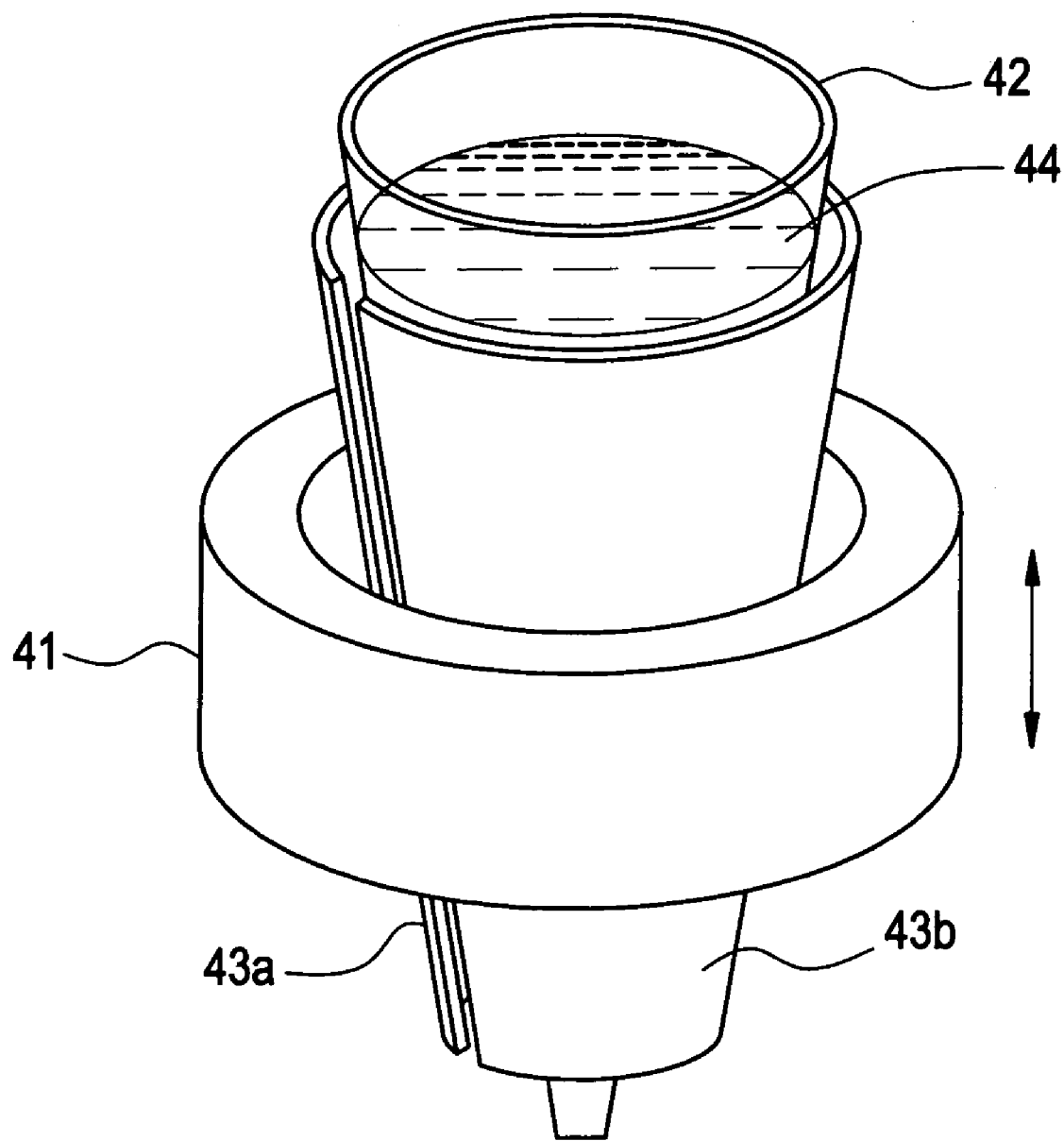
FIG. 17 shows the probe tip with the tip and capacitor electrodes inserted into the solenoid according to one embodiment of the present invention.

Now reference will be made to the non-limiting preferred embodiments shown in the FIGS. 15 to 17.

Figure 15:
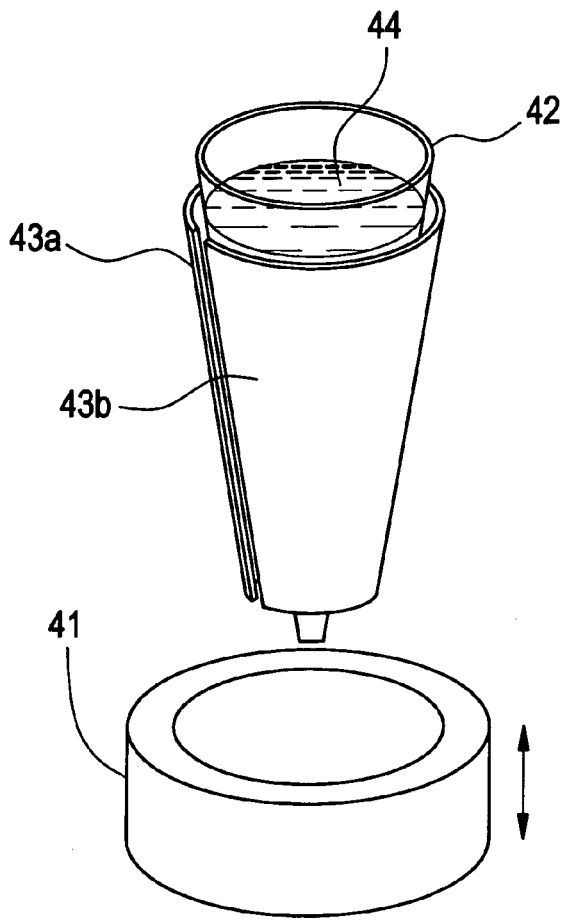
FIG. 15 shows perspective view of a probe tip, capacitor electrodes and solenoid according to a preferred embodiment of the present invention.

FIG. 15 shows one preferred embodiment in which the solenoid 41 is separated from the capacitive tip 42 having capacitor plates 43a and 43b. Assuming that the inductance of the solenoid is L=0.1 mH, the peak of the capacitor voltage (formula (7), with $\omega=2\pi f$) would occur at the frequency $$f_0 = \frac{1}{2\pi\sqrt{LC_0}} = \frac{1}{2\pi\sqrt{10^{-4} \cdot 2 \times 10^{-12}}} = 11.25 \text{ MHz} \quad (18)$$

Similarly, when the tip is filled with liquid 44, the frequency of the maximum capacitor voltage would be equal to:

$$f_{full} = \frac{1}{2\pi\sqrt{LC_{full}}} = \frac{1}{2\pi\sqrt{10^{-4} \cdot 15 \times 10^{-12}}} = 4.1 \text{ MHz} \quad (19)$$

The frequencies $f_0$ and $f_{full}$ may be too high to measure, especially with low-cost instruments. This can be rectified if a solenoid with higher inductance L is available. FIG. 16 shows a preferred embodiment in which the capacitive tip serves as a core. Since the electrodes of the capacitor are metal, the inductance can easily be ten or more times higher than the original value of L=0.1 mH for the solenoid only.

Thus, assuming that newly obtained inductance is L=1 mH, the frequencies $f_0$ and $f_{full}$ would be, respectively, 3.56 MHz and 1.3 MHz. These lower frequencies allow measurement of the capacitor voltages with lower cost electronic components. FIG. 17 shows a view of the preferred embodiment of FIG. 15 with the tip and electrodes inserted into the center of the solenoid.

The device of the present invention can also be used in any operation where precision measurement of liquids is required, particularly in connection with an analyzer for analyzing a sample, such as a blood, clinical or chemistry analyzer which are well known in the art and are described in such publications as U.S. Patent Publication Nos. 2003/0022380 A1 and 2003/0104634 A1 and WO 2004/027375, which are incorporated herein by reference in their entireties or an immunodiagnostic analyzer, such as described in U.S. Patent Publication No. 2004/0067164 which are incorporated herein by reference in their entireties. The analyzer includes a sample supply, optionally a reagent supply, a metering station that includes the apparatus described above and a measurement station and test elements, such as slides, cuvettes, or cups. In a preferred embodiment, the measurement station is a spectrophotomer, photometer, relectometer, electrometer or a luminometer for measuring chemiluminescence.

In some embodiments, the metering station for metering sample and reagent may be different. All these aspects of an analyzer are well known in the art and do not need to be described in detail.

The methods according to the present invention can be implemented by a computer program, having computer readable program code, interfacing with the computer controller of the analyzer as is known in the art.

It will be apparent to those skilled in the art that various modifications and variations can be made to the compounds, compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

We claim:

1. An apparatus for determining the volume of liquid in a probe tip of an aspirating or dispensing probe, comprising:
   two electrodes on opposite sides of the probe tip, wherein said electrodes and liquid form a variable capacitor;
   a resistor;
   a voltage source; said electrodes and resistor being in electrical communication in at least one of series, parallel or series and parallel to form an RC circuit; and
   a microprocessor in electrical communication with the RC circuit for converting an electrical signal to a volume of liquid in the probe tip.

2. An apparatus as claimed in claim 1, wherein the probe tip has a first larger end for fitting on the probe and a second smaller end having an opening for aspirating and dispensing a liquid, and wherein the electrodes are shaped to conform to the surface area of the probe between the first and second ends.

3. An apparatus for determining the volume of liquid in a probe tip of an aspirating or dispensing probe as claimed in claim 1, further comprising a solenoid, wherein the voltage source, electrodes, resistor, and solenoid are in electrical communication in at least one of series, parallel or series and parallel to form an RLC circuit, and the microprocessor is in electrical communication with the RLC circuit for converting an electrical signal to a volume of liquid in the probe tip.

4. A method for determining the volume of liquid having a known dielectric constant in a probe tip of an aspirating or dispensing probe, comprising:
   providing the apparatus according to claim 1;
   providing a liquid in the probe tip having a known dielectric constant;
   applying a known voltage (Ug) from the voltage source;
   measuring the voltage (U1) from the capacitor;
   determining the capacitance (C1) of the variable capacitor; and
   determining the volume (V2) of the liquid based on the capacitance (C2) and dielectric constant $\in$ of the liquid.

5. A method for determining the volume of liquid having a unknown dielectric constant in a probe tip of an aspirating or dispensing probe, comprising:
   providing the apparatus according to claim 1;
   providing a database or calibration curve of known capacitances versus known volumes for the liquid being measured or dispensed;
   providing the liquid in the probe tip;
   applying a known voltage (Ug) from the voltage source;
   measuring the voltage (U1) from the capacitor;
   determining the capacitance (C1) of the variable capacitor;
   comparing the capacitance (C1) with the known capacitances and volumes in the calibration curve or database;
   determining the volume of the liquid based on the comparison of the capacitance (C1) and the known capacitance.

6. A method for determining the presence of bubbles in a probe tip or of a desired volume of liquid is in the probe tip of an aspirating or dispensing probe, comprising:
   determining a reference capacitance (C1) of the desired volume of liquid (V1);
   providing the apparatus according to claim 1;
   providing a volume (V2) of liquid in the probe tip;
   applying a known voltage (Ug) from the voltage source;
   measuring the voltage from the capacitor (U2);
   determining the capacitance (C2) of the variable capacitor with volume (V2);
   comparing the determined capacitance (C2) with the reference capacitance (C1); and
   generating an error signal if the difference between the reference and determined capacitance exceeds a predetermined amount.

7. A method for determining the presence of bubbles in a probe tip or if a desired volume of liquid is in the probe tip of an aspirating or dispensing probe as claimed in claim 6, wherein the liquid has a known dielectric constant and the reference capacitance is calculated using the dielectric constant.

8. A method for determining the presence of bubbles in a probe tip or if a desired volume of liquid is in the probe tip of an aspirating or dispensing probe as claimed in claim 6, wherein the liquid has an unknown dielectric constant and the reference capacitance is determined from a database or calibration curve of known capacitances versus known volumes for the liquid.

9. An apparatus for dispensing or aspirating a liquid comprising:
   a probe;
   a probe tip adapted to fit on a first end of the probe to be inserted into a source of liquid;
   at least one of a vacuum or pressure source in fluid communication with the probe to produce a pressure differential with respect to ambient pressure, sufficient to at least one of aspirate or dispense a liquid respectively; and
   the apparatus for determining the volume of liquid in a probe tip as claimed in claim 1.

10. An apparatus as claimed in claim 9, further comprising a probe transport for moving the probe towards and away from the source of liquid.

11. An analyzer for analyzing an analyte in a sample comprising:
    a sample supply;
    a metering station for metering sample from the sample supply into or onto a test element, wherein the metering station comprises the apparatus for determining the volume of liquid in a probe tip of an aspirating or dispensing probe as claimed in claim 1; and
    a measurement station for measuring a property of the sample.

12. An analyzer as claimed in claim 11, further comprising a reagent source and a separate metering station for metering reagent.

13. An analyzer as claimed in claim 11, wherein the measurement station includes one or more of spectrophotomer, photometer, relectometer, electrometer or a luminometer.

14. A method for dispensing and aspirating a selected volume of a liquid comprising;
    providing a container containing the liquid to be aspirated;
    providing a probe having a vacuum and pressure source in fluid communication with the probe to produce a pressure differential with respect to ambient pressure, sufficient to aspirate and dispense the liquid, said probe being mounted for movement towards and away from the container;
    providing a probe tip adapted to fit on a first end of the probe to be inserted into the liquid;
    providing the apparatus for determining the volume of liquid in a probe tip as claimed in claim 1;

moving the probe in a direction towards the container until the distal end of probe tip is immersed in the liquid;

aspirating a volume (V1) of liquid into the probe tip;

determining the capacitance (C1) of the variable capacitor; and determining the volume (V2) of the liquid based on the capacitance (C2) and dielectric constant $\in$ of the liquid.

15. A method as claimed in claim 14, further comprising providing a detector for detecting when the probe tip approaches the liquid and stopping advancement of the probe tip upon entry into the liquid.

16. A method according to claim 14 implemented by a computer program interfacing with a computer.

17. An article of manufacture comprising a computer usable medium having computer readable program code configured to conduct the method of claim 14.

* * * * *